(12) United States Patent
Damasco et al.

(10) Patent No.: US 7,160,291 B2
(45) Date of Patent: *Jan. 9, 2007

(54) DETACHABLE CRYOSURGICAL PROBE

(75) Inventors: Sanford D. Damasco, Irvine, CA (US); Thach Duong, Tustin, CA (US)

(73) Assignee: Endocare, Inc., Irvine, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 10/828,031

(22) Filed: Apr. 20, 2004

(65) Prior Publication Data

US 2005/0010200 A1 Jan. 13, 2005

Related U.S. Application Data

(63) Continuation-in-part of application No. 10/603,883, filed on Jun. 25, 2003.

(51) Int. Cl.
*A61B 18/02* (2006.01)
(52) U.S. Cl. .......................................... 606/23; 606/20
(58) Field of Classification Search ............. 606/20–26
See application file for complete search history.

(56) References Cited

U.S. PATENT DOCUMENTS

| | | | |
|---|---|---|---|
| 3,524,446 A * | 8/1970 | Crump et al. ................. | 606/25 |
| 4,018,227 A * | 4/1977 | Wallach ........................ | 606/23 |
| 4,206,760 A * | 6/1980 | Davis ............................ | 606/23 |
| 5,224,943 A * | 7/1993 | Goddard ....................... | 606/20 |
| 5,254,116 A * | 10/1993 | Baust et al. .................. | 606/23 |
| 5,281,213 A * | 1/1994 | Milder et al. ................. | 606/15 |
| 5,452,582 A * | 9/1995 | Longsworth ................ | 62/51.2 |
| 5,520,682 A * | 5/1996 | Baust et al. .................. | 606/24 |
| 5,800,487 A | 9/1998 | Mikus ......................... | 607/105 |
| 5,910,104 A | 6/1999 | Dobak ......................... | 600/121 |
| 5,978,697 A | 11/1999 | Maytal ........................ | 600/411 |
| 5,992,158 A * | 11/1999 | Goddard et al. ............. | 62/51.2 |
| 6,106,517 A * | 8/2000 | Zupkas ........................ | 606/20 |
| 6,306,129 B1 | 10/2001 | Little ........................... | 606/23 |
| 6,374,619 B1 * | 4/2002 | Bessendorf ................ | 62/51.2 |
| 6,755,823 B1 * | 6/2004 | Lalonde ...................... | 606/23 |
| 6,786,902 B1 * | 9/2004 | Rabin et al. .................. | 606/23 |
| 2002/0022832 A1 | 2/2002 | Mikus ......................... | 606/20 |
| 2002/0188287 A1 * | 12/2002 | Zvuloni et al. ............... | 606/21 |
| 2003/0055415 A1 | 3/2003 | Yu ............................... | 606/21 |
| 2003/0055416 A1 | 3/2003 | Bui .............................. | 606/21 |
| 2003/0078570 A1 * | 4/2003 | Heiner et al. ................ | 606/21 |
| 2003/0195605 A1 * | 10/2003 | Kovalcheck et al. ........ | 607/138 |
| 2004/0049177 A1 * | 3/2004 | Zvuloni et al. ............... | 606/21 |

\* cited by examiner

*Primary Examiner*—Henry M Johnson, III
(74) *Attorney, Agent, or Firm*—Lawrence N. Ginsberg

(57) ABSTRACT

A cryosurgical probe system includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly. The cryosurgical probe system includes the capability of providing return fluid flow.

50 Claims, 13 Drawing Sheets

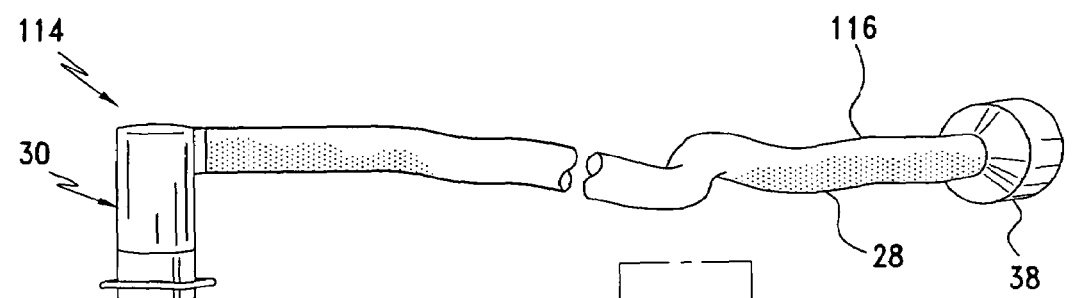
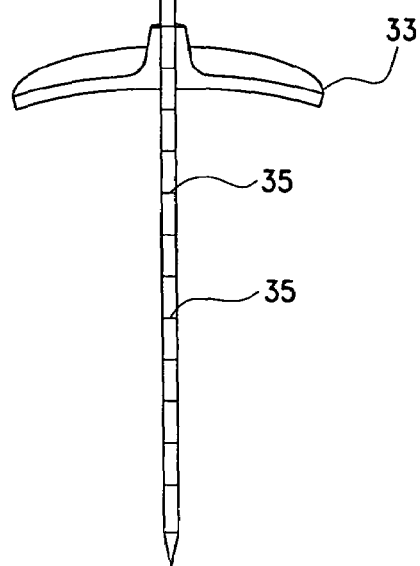
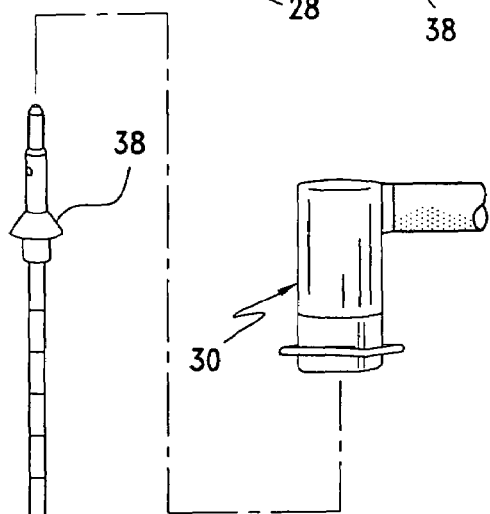
FIG. 5
FIG. 6

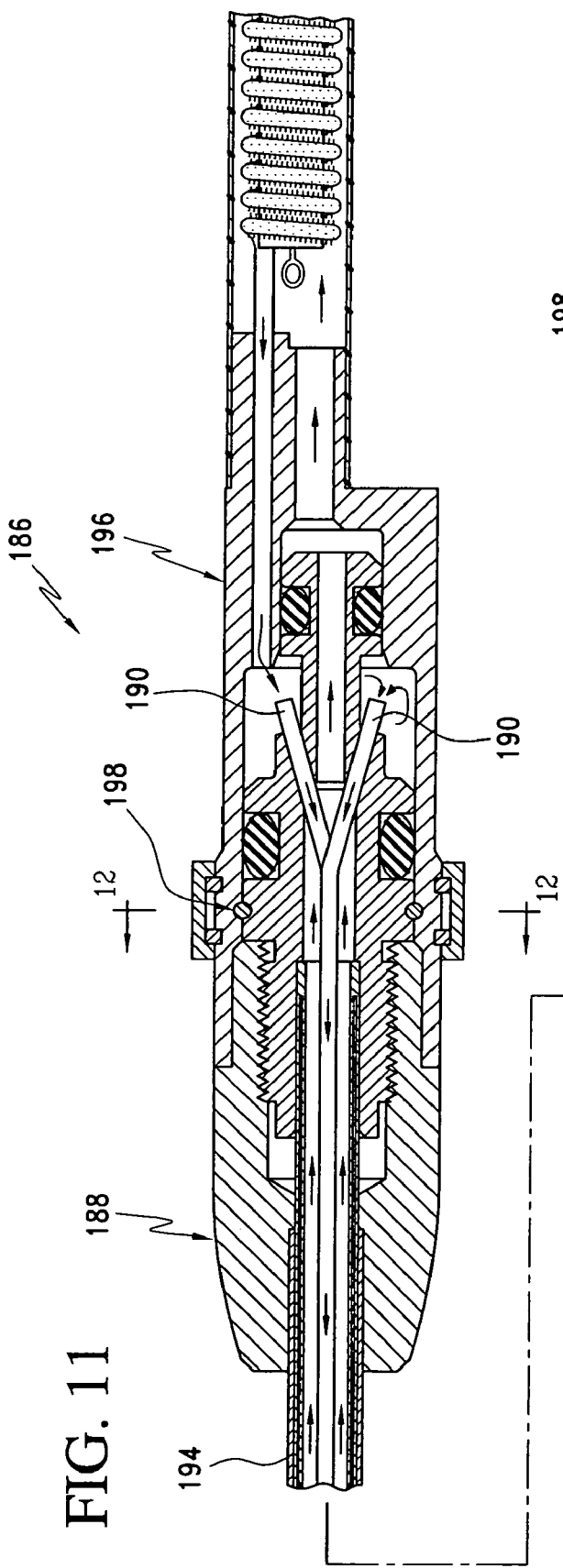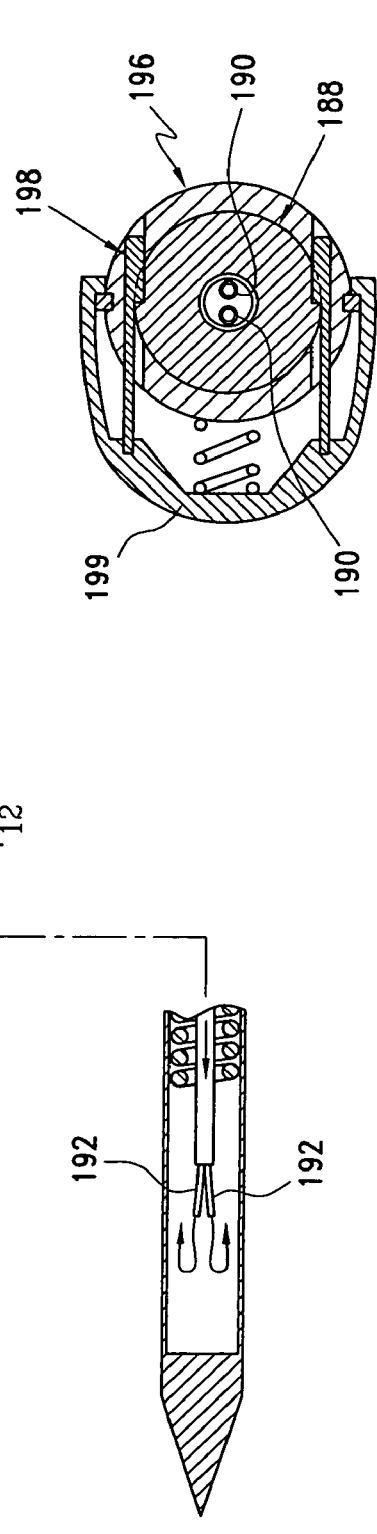
FIG. 11
FIG. 12

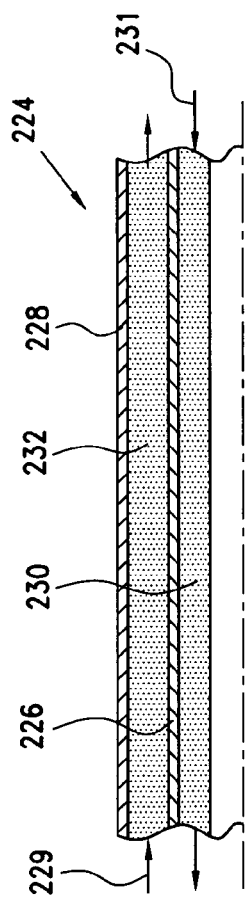
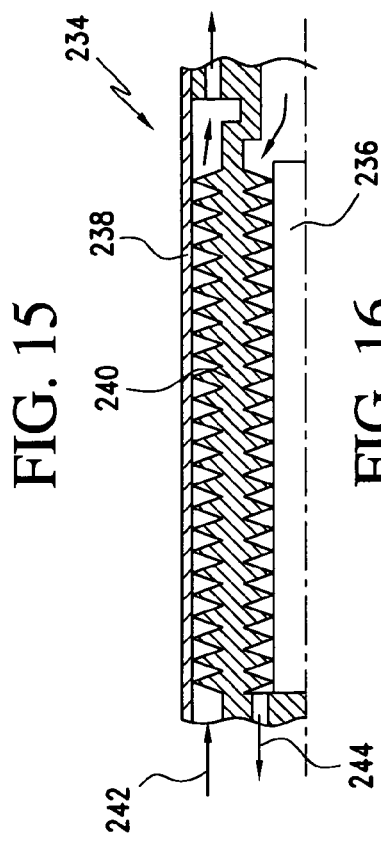
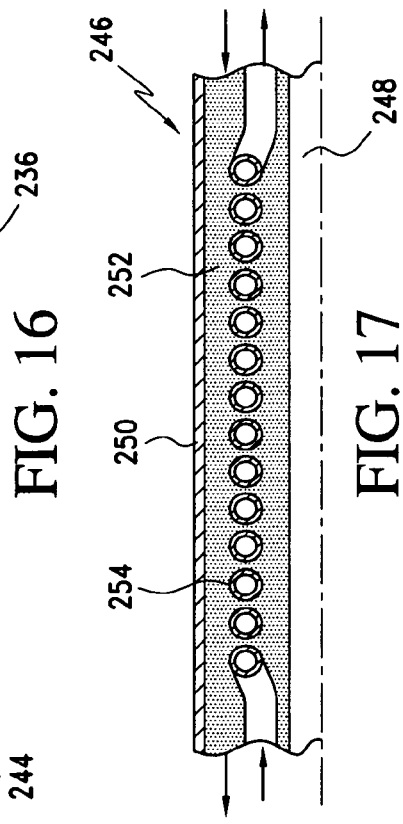
FIG. 15
FIG. 16
FIG. 17

DETACHABLE CRYOSURGICAL PROBE

CROSS REFERENCE TO RELATED APPLICATIONS

This is a continuation-in-part of U.S. Ser. No. 10/603,883, entitled Detachable Cryosurgical Probe, filed Jun. 25, 2003.

BACKGROUND OF THE INVENTION

1. Field of the Invention

The present invention relates to cryosurgical probes and more particularly to a detachable cryosurgical probe.

2. Description of the Related Art

Cryosurgery involving the use of a cryosurgical probe assemblies typically involves the use of cryoprobes that are each attached to a handle that are, in turn, connected to a high-pressure fluid line with a quick-disconnect for attachment to a fluid source. There is an inherent problem with this type of system inasmuch as each cryosurgical probe assembly should be used only once due to sterilization and performance factors. Therefore, typically, the entire cryosurgical probe assembly and high-pressure fluid line must be discarded after that single use. Due to these sterilization/performance requirements there is a need to assure that the cryosurgical probe assembly may be rendered non-useable after a single-use.

Previous attempts to mitigate this problem have involved utilizing a disposable sheath over a cryosurgical probe. For example, U.S. Pat. No. 5,910,104, issued to J. D. Doback, III et al, discloses a disposable, sterilizable sheath for use on a closed loop Joule-Thomson cryosurgical probe, and the combination of the disposable sheath and the closed loop probe. The sheath is slipped over the probe, thereby separating the probe from the environment. The sheath has a grip that fits over the handle of the cryosurgical probe. The sheath has a hollow multi-lumen catheter shaped and sized to fit snugly over the cannula of the cryosurgical probe.

U.S. Pat. No. 6,306,129 B1, issued to Little et al, also discloses the use of a disposable sheath over a cryosurgical probe.

Similarly, U.S. Pat. Publication 2002/0022832 A1, to Mikus et al, discloses a cryoprobe assembly that includes a cryoprobe and an outer sheath assembly detachably connected thereto.

Although cryosurgical probes have been very successfully used for treating prostate cancer their use has been somewhat limited for other applications such as liver, kidney, etc. because of the difficulty of imaging those body parts using ultrasound. Ultrasound is presently the preferred imaging instrumentality for prostate cryosurgery. It can be successfully used because the rectum, which is amenable to ultrasound imaging device insertion, is adjacent to the prostate. Thus, iceball formation can be effectively monitored. The liver, kidney, breast, etc. cannot be as conveniently monitored. Thus, it is desired that other imaging techniques be used. However, presently designed cryosurgical probes are not convenient with, for example, computerized tomography (CT) applications because the probe, including its handle and fluid line connection, are generally disposed along a single direction. This is problematic given the space considerations present with CT devices.

U.S. Pat. No. 5,978,697, issued to Maytal, et al, discloses an MRI-guided cryosurgical system. The Maytal system includes: (a) an MRI magnet for accommodating a patient, the MRI magnet having at least one opening for enabling access of a surgeon to the patient, the MRI magnet including at least one channel extending therethrough for receiving a line member of a surgical device; (b) a surgical device, including: (i) an operating member for operating the patient; (ii) a control member for controlling the operating member, the control member being positioned externally to the MRI room; and, (iii) a line member having a first end connectable to the operating member and a second end connectable to said control member, wherein at least a portion of the line member is received within the channel of the MRI magnet.

What is desired is a cryosurgical probe in which the operative portion of the cryosurgical probe is detachable. It is also desired that a cryosurgical probe be provided that can be used in conjunction with a variety of imaging devices.

SUMMARY OF THE INVENTION

In a broad aspect, the present invention is embodied as a cryosurgical probe system that includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly.

The fluid connector assembly includes a substantially cylindrical lock housing securely attached to the outlet section of the fluid supply line, the lock housing having a fluid inlet conduit for receiving high pressure fluid from the fluid supply line and a fluid outlet conduit for transferring return fluid from the cryosurgical probe to the fluid supply line. A locking mechanism is positioned at a locking portion of the lock housing to provide detachable engagement of a cryosurgical probe positioned therein.

The detachable cryosurgical probe receives fluid from the fluid connector assembly and manipulates the fluid to provide suitable temperatures for cryosurgical treatment. It includes a fluid delivery/return manifold assembly having a fluid delivery section and a return manifold section. The return manifold section is positioned over a portion of the fluid delivery section. The return manifold section includes an insulative vacuum sleeve. The fluid delivery/return manifold assembly has a proximal end section. An outer sheath is securely positioned over the vacuum sleeve and extends from the fluid delivery/return manifold assembly. A lock anchor is securely positioned over the outer sheath. The lock anchor provides detachable connection to the fluid connector assembly of a detachable cryosurgical system.

During operation fluid is delivered through the fluid delivery/return manifold assembly, through a Joule-Thomson (J-T) port defined at a distal end of the fluid delivery section and is returned through the return manifold section and delivered out of the cryosurgical probe. The insulative vacuum sleeve is provided between the outer sheath and the return manifold section at a control region of the outer sheath proximal to a distally located treatment region of the outer sheath.

Unlike previous cryosurgical probe systems, the operative portion of the present system, i.e. the detachable cryosurgical probe, can be discarded after a single use. However, the fluid supply line and the connector assembly can be reused.

The cryosurgical probe system includes the capability of providing return fluid flow. Suitable passageways in the detachable cryosurgical probe and the fluid connector assembly provide this feature.

BRIEF DESCRIPTION OF THE DRAWINGS

FIG. 5 is a perspective illustration of the cryosurgical probe inserted within the connector assembly.

FIG. 6 is a perspective illustration of the cryosurgical probe detached from the connector assembly.

FIG. 10A is an enlarged view of a portion of FIG. 10.

FIG. 11 is a cross-sectional view of an embodiment of the cryosurgical probe system in which two Joule-Thomson nozzles are utilized, this embodiment being further differentiated by the use of a pushbutton/pin assembly to secure the connector assembly relative to the cryosurgical probe.

FIG. 12 is view taken along line 12—12 of FIG. 11.

FIG. 15 is a cross-sectional view of a portion of a tube-in-tube sintered cryostat that may be used in lieu of the finned cryostat illustrated in the previous embodiments.

FIG. 16 is a cross-sectional view of a portion of a threaded cryostat.

FIG. 17 is a cross-sectional view of a portion of a coiled/sintered cryostat.

DETAILED DESCRIPTION OF THE INVENTION

Figure 1:
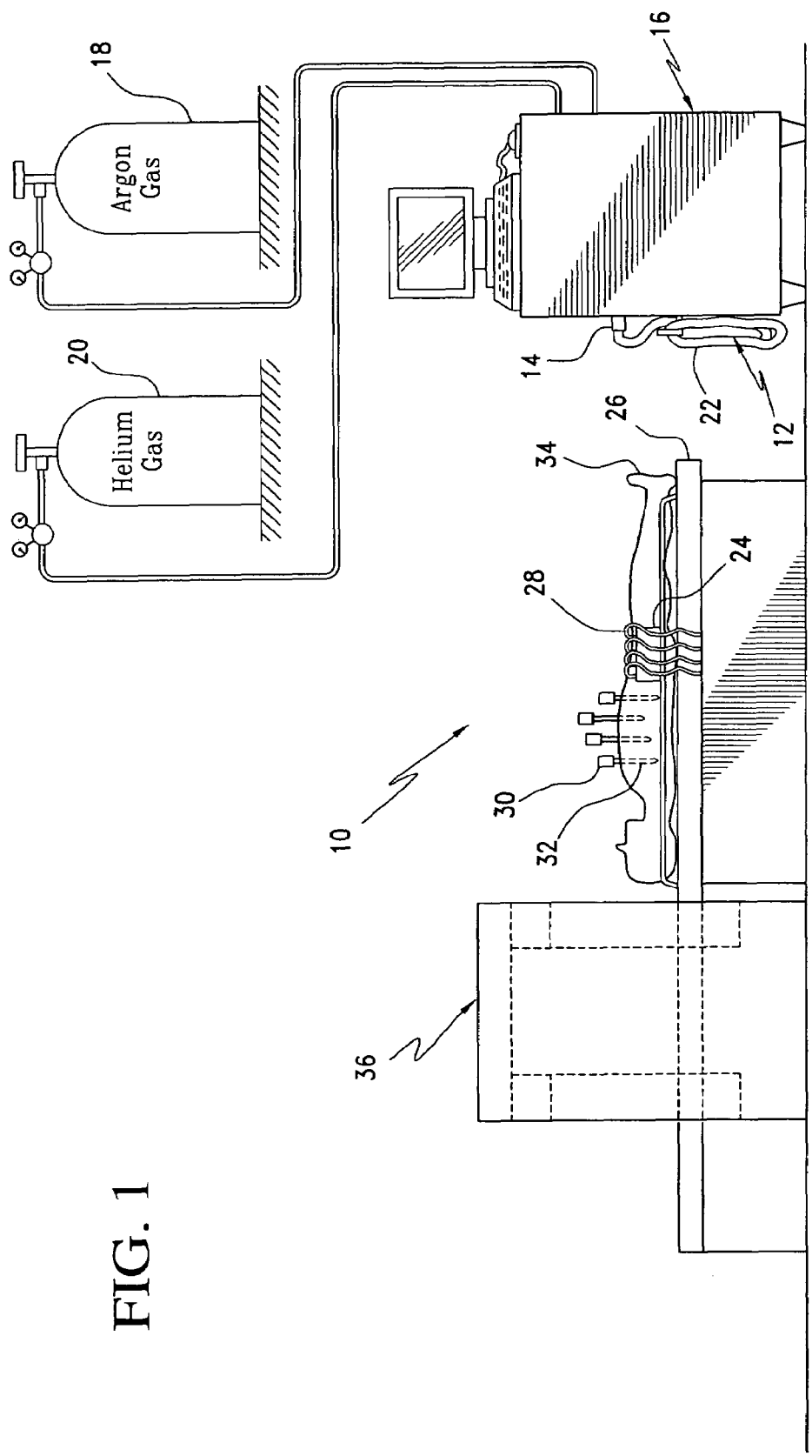
FIG. 1 is an overall system schematic of the cryosurgical probe system of the present invention, showing an environment with a patient positioned on a CT table prior to connection of the fluid lines and prior to being introduced into the CT device.

Referring now to the drawings and the characters of reference marked thereon, FIG. 1 illustrates a preferred embodiment of the cryosurgical probe system of the present invention, designated generally as 10. The cryosurgical probe system 10 includes a fluid supply line 12 that is connected at an inlet section 14 to a source 16 of cryogenic fluid. The fluid source 16 may be, for example, a cryosurgical system such as that manufactured by present assignee, Endocare, Inc., Irvine, Calif. Such a cryosurgical system typically utilizes argon gas from an argon gas source 18 to provide Joule-Thomson cooling of the cryosurgical probes. Alternatively, nitrogen can be used. Alternatively, a fluid supply system can be utilized that does not require an external fluid supply source. Heating of the cryosurgical probes is typically provided by a helium gas source 20 for providing a helium gas flow through the Joule-Thomson nozzle of the cryosurgical probe. This provides a heating effect. Such heating of the cryosurgical probes is provided to unstick the probes from the treated tissue for cryoprobe removal. Alternatively, other methods for warming may be used such as electrical heating via heated coils, microwave or RF heating.

The fluid supply line 12 preferably includes a manifold-system hose 22 for providing a connection from the source 16 to a manifold 24. The manifold 24 may be connected to a rail or otherwise to a CT table 26. Manifold-fluid connector assembly hoses 28 of the fluid supply line 12 provide fluid connections between fluid connector assemblies 30 and the manifold 24. The fluid connector assemblies 30 provide attachment to the detachable cryosurgical probes 32.

FIG. 1 illustrates a patient 34 positioned on a CT table 26 adjacent to a CT device 36. The cryosurgical probes 32 have been inserted in treatment zones for cryosurgical treatment. The hoses 28 are not yet connected to the manifold 24. It is assumed that prior to probe insertion shown in FIG. 1 that the tumor location has been confirmed under imaging guidance (e.g. CT, ultrasound, etc.).

Figure 2:
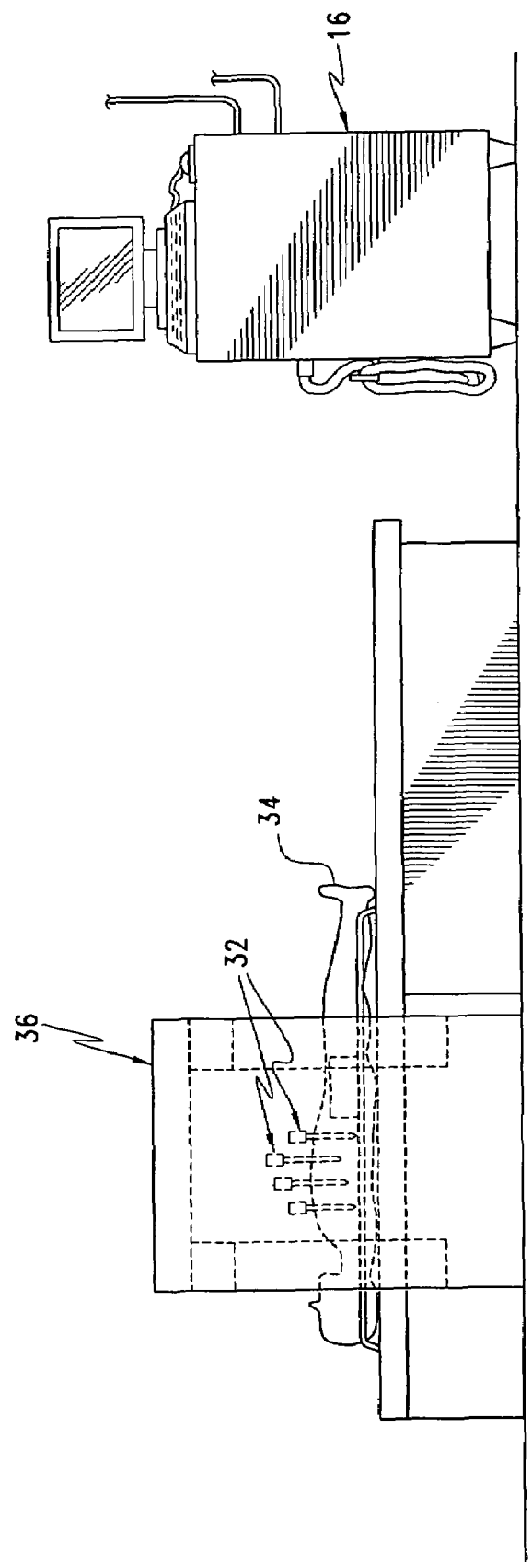
FIG. 2 is an overall system schematic showing a patient introduced into the CT device but prior to cryosurgical treatment.

Referring now to FIG. 2, the patient 34 is introduced into the imaging section of the CT device 36 and scans are taken with the cryosurgical probes 32 inserted. These initial scans are made to assure that the tips of the cryosurgical probes 32 are properly positioned per a treatment plan.

Figure 3:
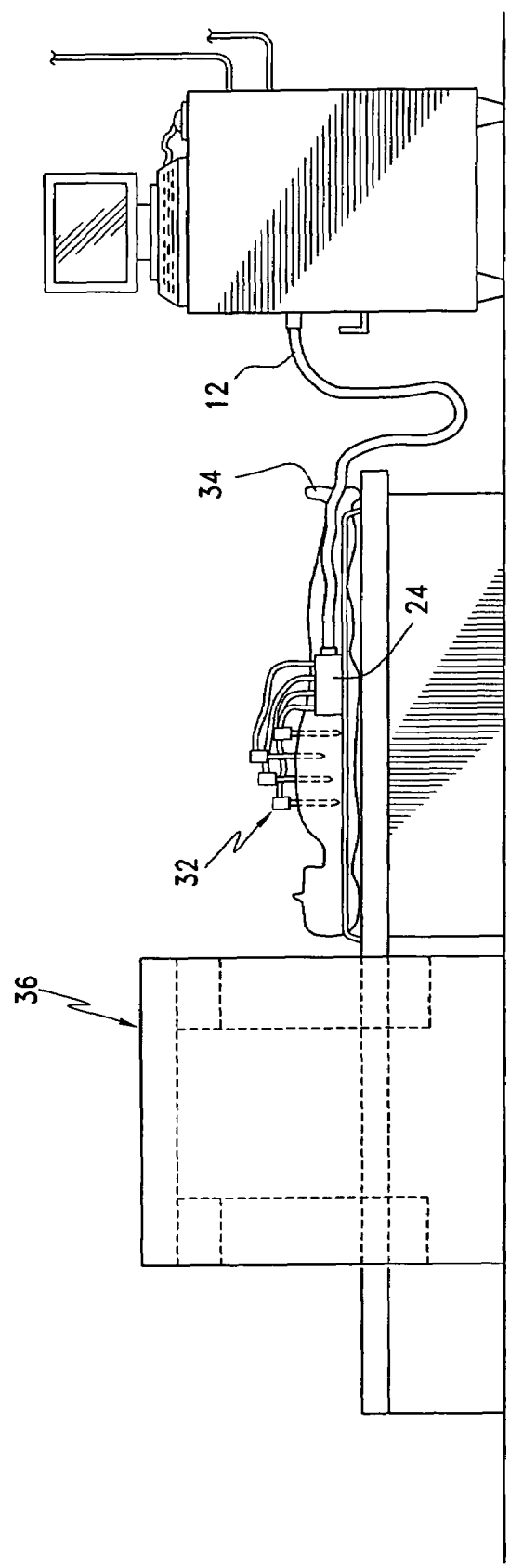
FIG. 3 shows the patient positioned away from the CT device and the cryosurgical probes attached to a manifold in preparation for cryosurgery.

Referring now to FIG. 3, the patient 34 is shown positioned away from the imaging section of the CT device 36 and the cryosurgical probes 32 are attached to the manifold 24 in preparation for cryosurgery.

Figure 4:
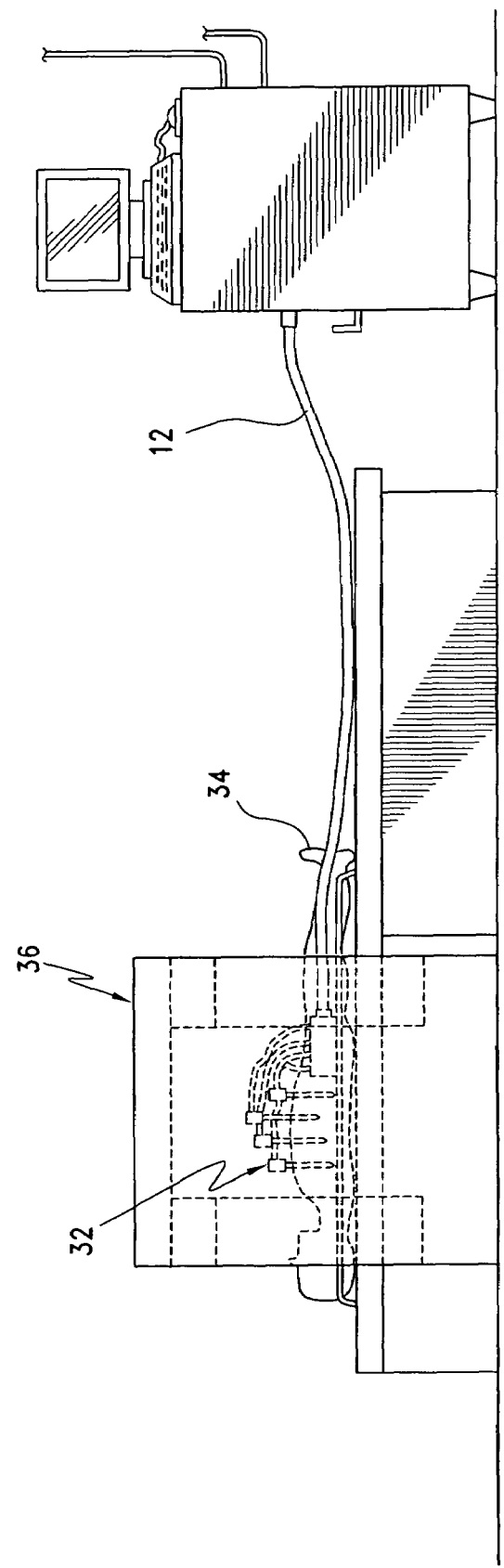
FIG. 4 shows the patient introduced to the CT device and cryosurgery being performed under CT scanning guidance.

As shown in FIG. 4, the patient is then again introduced to the device 36 and cryosurgery is performed under CT scanning. This allows for the monitoring of the iceballs formed during this procedure. There are typically two freeze-thaw cycles included in a cryosurgical treatment.

Referring now to FIG. 5, a cryosurgical probe 32 is shown inserted within its connector assembly 30. A manifold-fluid connector assembly hose 28 is shown with appropriate connector 38 for connection to the manifold 24. The cryosurgical probe 32 preferably includes a slideable wedge element 33 that can be used as a marker for assuring that the correct depth of the cryosurgical probe 32 is maintained. Furthermore, the bottom of the wedge element 33 contacts the body of the patient 34 to decrease the probability of accidental translation of the cryosurgical probe 32. Spaced markings 35 may be provided on the outer surface of the cryosurgical probe 32. These markings 35 may be, for example, at 1 cm intervals.

Referring now to FIG. 6, the cryosurgical probe 32 is shown detached from its connector assembly 30. As can be seen in this figure, and described in detail below, the detachable cryosurgical probe 32 includes a radially extending hub 38 that provides attachment to the connector assembly 30.

Figure 7:
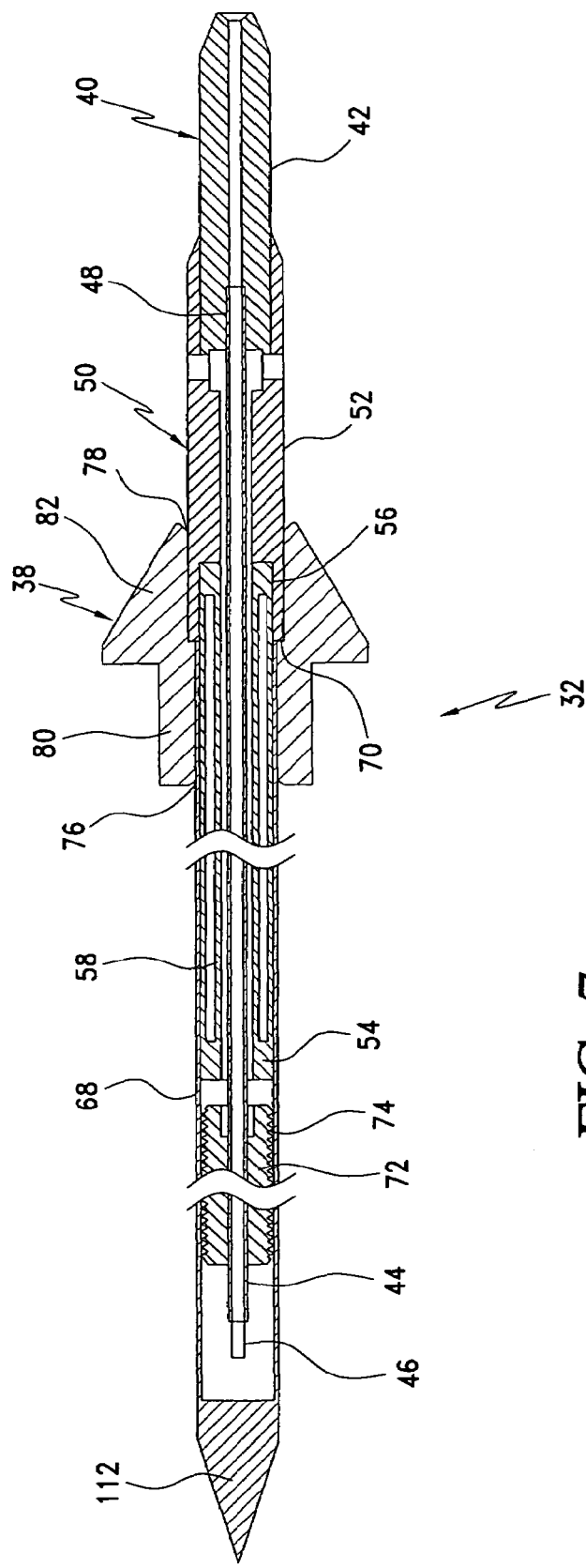
FIG. 7 is a cross-sectional view of the cryosurgical probe.

Referring now to FIG. 7, a preferred embodiment of the cryosurgical probe 32 is illustrated. The cryosurgical probe 32 includes a fluid delivery assembly, designated generally as 40. The fluid delivery assembly 40 includes a high pressure stem 42, an extension tube 44 and an orifice tube 46. The high pressure stem 42 has a proximal end section that receives high pressure fluid from the fluid connector assembly 30. The extension tube 44 is welded, at a first end

48, to the high pressure stem. The extension tube 44 is in fluid communication with the high pressure stem 42. The orifice tube 46 is secured to a second end of the extension tube 44. The orifice tube 46 is in fluid communication with the extension tube 44. The orifice tube 46 comprises a Joule-Thomson (J-T) port at a distal end thereof.

The cryosurgical probe 32 includes a return manifold assembly, designated generally as 50. The return manifold assembly 50 includes a low pressure stem 52 and a vacuum tube 54. The low pressure stem 52 is positioned about an outer surface of the high pressure stem 40 and is securely connected to the high pressure stem 40. It may be secured via threads and adhesive or by welding. The vacuum tube 54 is secured at an end 56 to the low pressure stem 52. The vacuum tube 54 has a desired insulative air gap 58 formed therein. The air gap 58 provides selected non-cooling areas of the cryosurgical probe 32.

An outer sheath 68 is securely positioned over the return manifold assembly 50. The outer sheath 68 is a cylindrical tube preferably formed of stainless steel which provides the desired heat transfer characteristics. The outer sheath 68 is welded to the low pressure stem 52 at location 70. It is pointed at its closed distal end to provide insertion to the treatment area tissue. The outer sheath 68 includes a cylindrical collector 72 having external threads 74 that cooperate with the cylindrical tube 68 to guide the return fluid from the J-T port 46 to the vacuum tube 54, as will be explained below in detail.

The hub 38 is securely positioned over the outer sheath 68 and the return manifold assembly 50. The hub 38 is securely connected at weld location 76 to the outer sheath 68 and at weld location 78 to the low pressure stem 52. The hub 38 includes a cylindrical portion 80 and a tapered extension 82 extending therefrom. The tapered extension 82 has a radial extending portion. The cylindrical portion 80 is securely attached to the outer sheath 68 and the tapered extension is securely attached to the low pressure stem 52.

Figure 8:
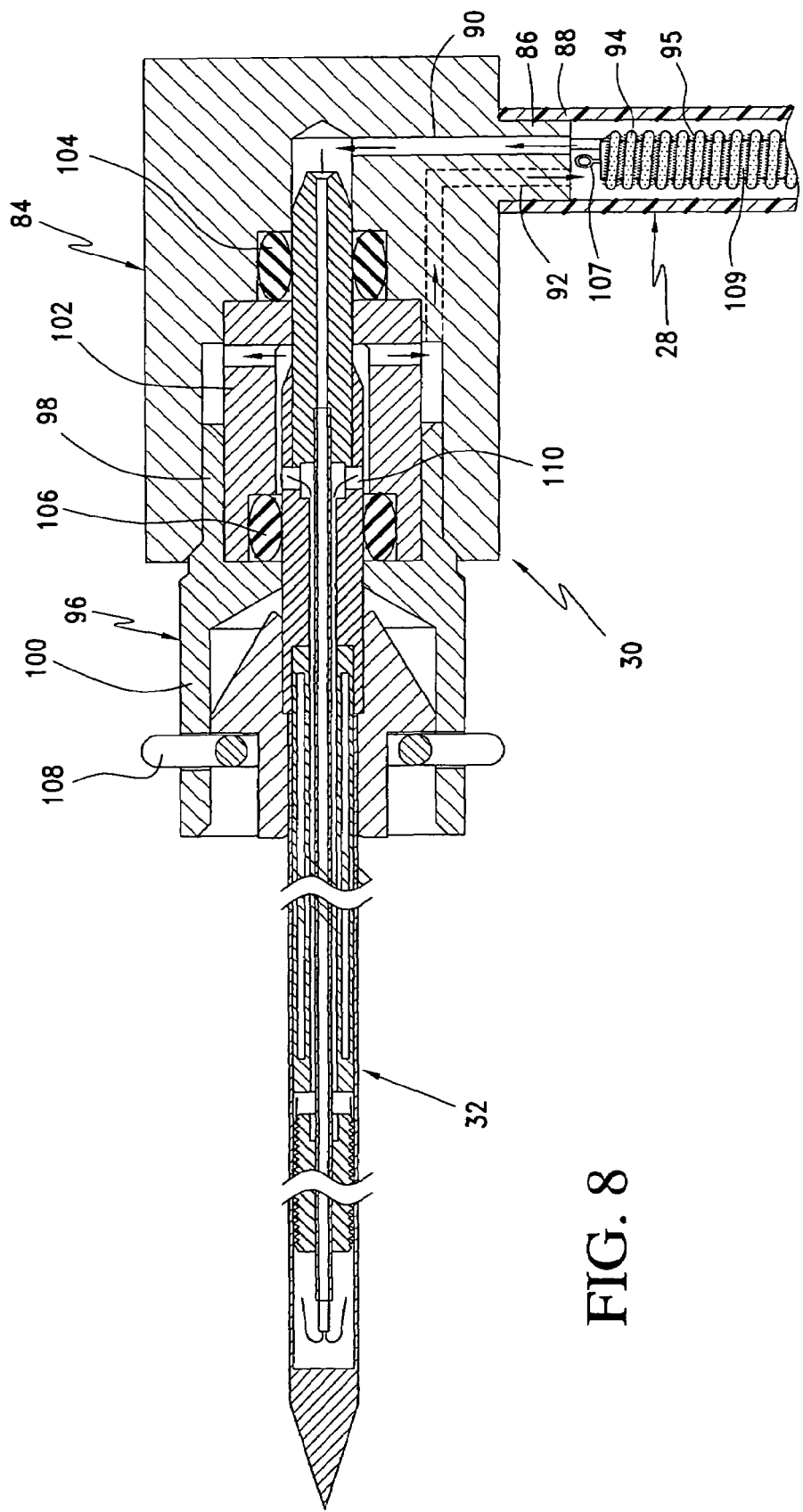
FIG. 8 is a cross-sectional view of the cryosurgical probe inserted within the connector assembly.

Referring now to FIG. 8, the cryosurgical probe 32 is shown inserted into the connector assembly 30. The connector assembly 30 includes a substantially cylindrical connector housing 84 having a radially extending boss 86 securely attached to the outlet section 88 of the manifold-fluid connector assembly hose 28 of the fluid supply line 12. The connector housing 84 has a fluid inlet conduit 90 for receiving high pressure fluid from the fluid supply line 12 and a fluid outlet conduit 92 for transferring return fluid from the cryosurgical probe 32 to the fluid supply line 12. The connector housing 84 has a central axis parallel to the cryosurgical probe 32. The radially extending boss 86 is at substantially 90 degrees relative to that central axis to maintain the supply line closer to the patient, which is advantageous for CT related applications due to the space limitations. A cryostat 94 is positioned in the manifold-fluid connector assembly hose 28. The cryostat 94 preferably has fins 95.

The fluid connector assembly includes a lock housing 96, which is securely positioned within an axial opening of the connector housing 84. The lock housing 96 has a cylindrical portion 98 and a locking portion 100. A spacing element 102 axially positions the lock housing 100 relative to the connector housing 84 and radially positions the detachable cryosurgical probe 32 relative to the lock housing 96.

A high pressure seal 104 is positioned relative to the cryosurgical probe 32, the connector housing 84 and the spacing element 102 to contain the high pressure fluid within the connector housing 84 and enable the high pressure fluid to be delivered to the cryosurgical probe 32.

A low pressure seal 106 is positioned relative to the cryosurgical probe 32, the spacing element 102, and the lock housing 100 to prevent return fluid leakage.

A locking spring 108 is positioned in the locking portion 100 of the lock housing 96 to provide detachable engagement of a cryosurgical probe positioned therein.

Positioned within the connector assembly 30 is a thermocouple 107. The thermocouple 107 is contained within a thermocouple housing tube 109 for providing temperature data. The thermocouple housing tube 109 supports the cryostat 94.

During operation, with the cryosurgical probe positioned within the connector assembly 30, cryogenic fluid originating from the argon tank 18 flows through the manifold-fluid connector assembly hose 28 within the cryostat 94 and through the conduit 90 in the connector housing 84. The flow is re-directed approximately 90 degrees, flows through the central passageway in the high pressure stem 42, through the extension tube 44, through the orifice tube 46, and out of the J-T port.

After being expelled from the J-T port the return fluid is directed between the threads 74 of the cylindrical collector 72 and the outer sheath 68. (The cylindrical collector 72 is not threaded into the outer sheath 68 and therefore the threads 74 provide a path for fluid flow.) The return flow then travels in the space between the inner surface of the vacuum tube 54 and the outer surface of the extension tube 44. It then flows through openings 110 in the low-pressure stem 52 through the spacing element 102 and through the fluid outlet conduit 92 in the connector housing 84. The return fluid is then expelled through the manifold-fluid connector assembly hose 28.

In the device illustrated the cryosurgical probe 32 is shown with a pointed tip 112 to provide insertion into the patient's tissue for the desired application. However, it is understood that the tip may be blunt, depending on the application. For example, for certain applications direct insertion is desirable. For other applications, insertion via a cannula/introducer is preferred.

Although application of this device utilizing CT guidance has been discussed, the cryosurgical probe 32 may be used with a variety of guidance tools, such as MRI and ultrasound. In one preferred implementation ultrasound is used for initial guidance, followed up with CT for final confirmation.

Although the present invention has been discussed above with respect to a cryosurgical probe having a rigid outer sheath, the cryosurgical probe may be made to be malleable by including at least one malleable segment thereon. Malleable segments are formed of material that permit reshaping and bending to reposition the ablating surface for greater ablation precision. An example of a cryosurgical probe having malleable characteristics is disclosed and claimed in our co-pending patent application Ser. No. 09/957,337, Pub. No. US 2003/0055415 A1, filed on Sep. 20, 2001 entitled Malleable Cryosurgical Probe, incorporated in its entirety herein by reference.

One method for providing malleable characteristics includes providing a malleable shaft with a bellows portion. Our co-pending patent application Ser. No. 10/057,033, Pub. No. US 2003/0055416 A1, filed on Jan. 23, 2002 entitled Cryosurgical Probe With Bellows Shaft, incorporated in its entirety herein by reference, discloses use of a bellows portion for providing the necessary reshaping and bending.

Although the cryosurgical probe has been shown as having approximately a 90 degree extension from the point where the manifold-fluid connector assembly hoses 28 connect it is understood that this angle can vary depending on the desired application. The desired connection angle may be, for example, in a broad range of from 0 degrees to 180 degrees (i.e. there may not be a bend). A preferred range is about 80 degrees to about 140 degrees.

If the detachable cryosurgical probe is utlilized in combination with ultrasound the outer sheath may have an echogenic coating with, for example, a porous microstructure having the ability to trap microscopic air bubbles. This creates thousands of highly efficient ultrasound reflectors on the surface of the sheath.

Figure 9:
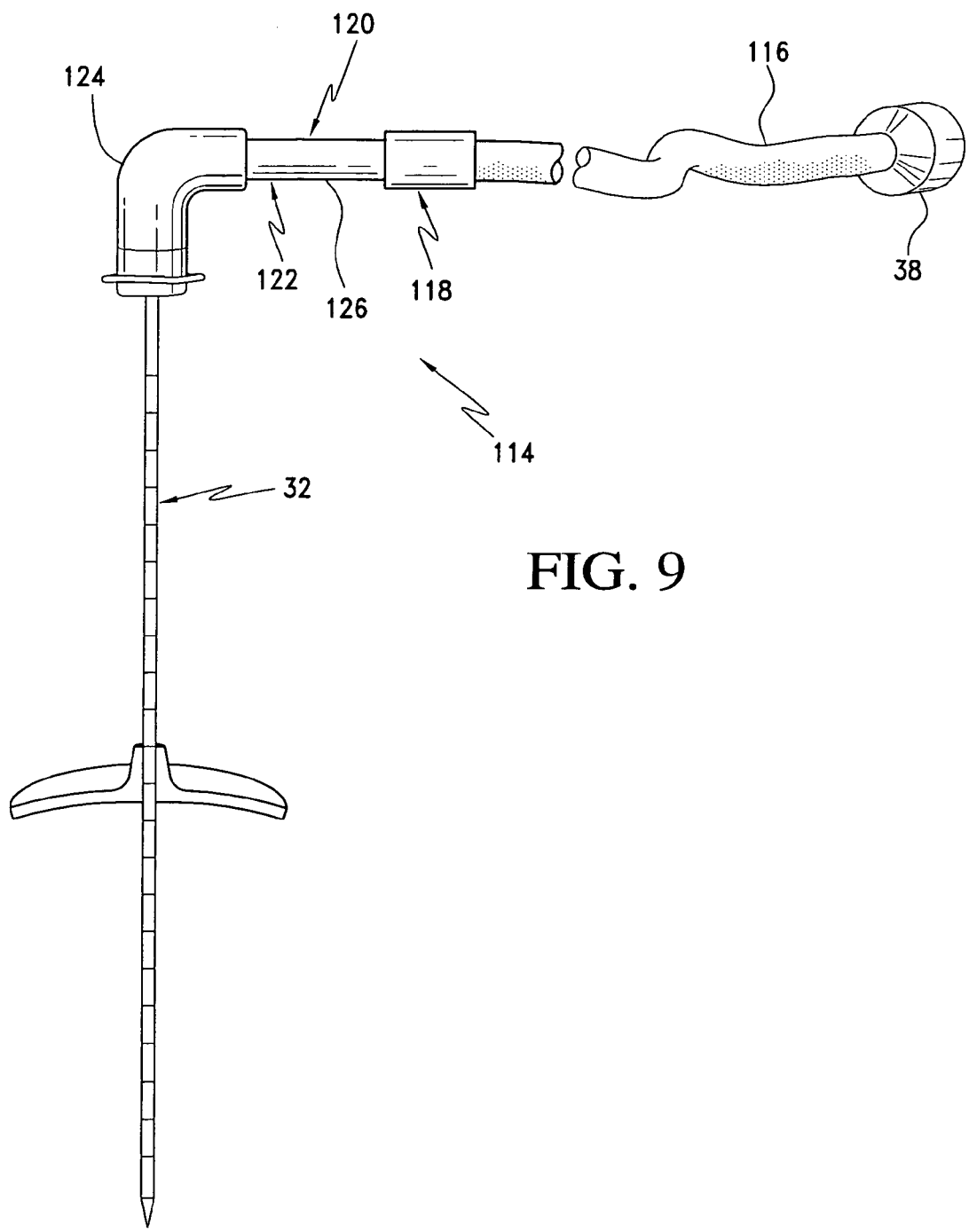
FIG. 9 shows an alternative embodiment of the cryosurgical probe in which a rigid curved portion is utilized and a connector assembly positioned proximal to the rigid curved portion.

Referring now to FIG. 9, another embodiment of the cryosurgical probe system is illustrated, designated generally as 114. In this embodiment, a fluid supply line 116 is connectable at an inlet section to a source of cryogenic fluid (not shown). A fluid connector assembly 118 is securely connected to an outlet section of the fluid supply line 116 for receiving fluid from the outlet section of the fluid supply line 116. A detachable cryosurgical probe 120 is detachably connectable to the fluid connector assembly 118. The cryosurgical probe 120 receives fluid from the fluid connector assembly 118. In this embodiment, the cryosurgical probe 120 includes an angled extension assembly 122. Angled extension assembly 122 includes an angled portion 124 and extension portion 126. The angled extension assembly 122, in this embodiment, provides the ability to connect the fluid supply line 116 to the cryosurgical probe 120 without effecting the probe position within the patient (which has already been confirmed under image guidance).

Figure 10:
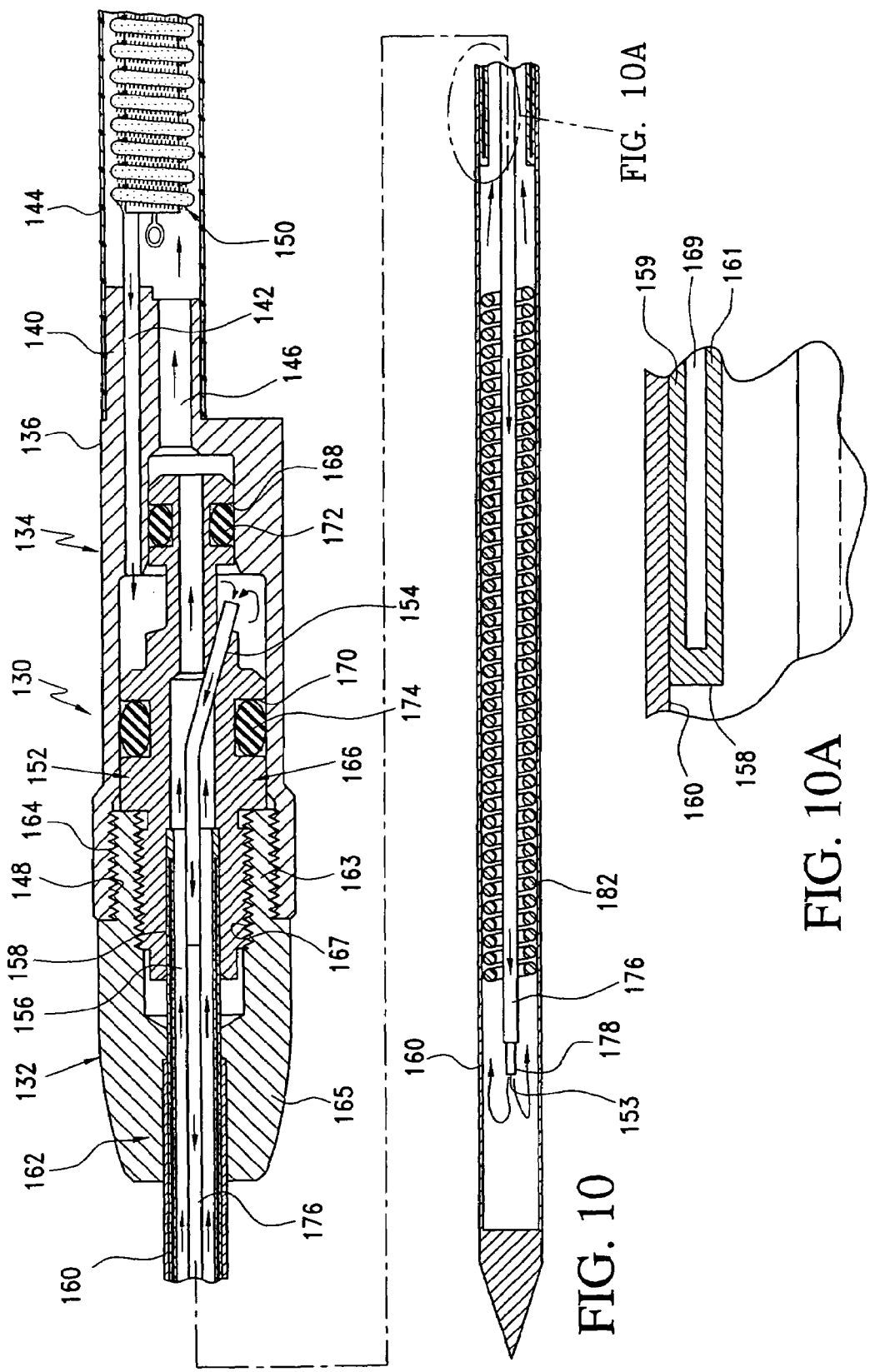
FIG. 10 is a cross-sectional view of an embodiment of the cryosurgical probe system in which threads are utilized to secure the connector assembly relative to the cryosurgical probe.

Referring now to FIG. 10, another embodiment of the cryosurgical probe system is illustrated, designated generally as 130. A cryosurgical probe 132 is shown inserted into a fluid connector assembly 134. The connector assembly 134 includes a substantially cylindrical lock housing 136 having an axially extending boss 140 securely attached to the outlet section 144 of a fluid supply line. The lock housing 136 has a fluid inlet conduit 142 for receiving high pressure fluid from the fluid supply line and a fluid outlet conduit 146 for transferring return fluid from the cryosurgical probe 132 to the fluid supply line. A locking mechanism such as internal threads 148 provides secure attachment to the cryosurgical probe 132.

The fluid supply line includes a cryostat assembly 150 positioned adjacent to the outlet section 144. The cryostat assembly 150 may comprise one or a plurality of cryostats.

The cryosurgical probe 132 includes a fluid delivery/return manifold assembly, designated generally as 152. The fluid delivery/return manifold assembly 152 includes a fluid delivery section 154 and a return manifold section 156. The return manifold section 156 is positioned over a portion of the fluid delivery section 154. The return manifold section 156 includes an insulative vacuum sleeve 158. The vacuum sleeve 158 essentially comprises an outer tube 159 surrounding an inner tube 161 with a vacuum gap 169 therebetween.

An outer sheath 160 of the cryosurgical probe 132 is securely positioned over the vacuum sleeve 158 and extends from the fluid delivery/return manifold assembly 152.

It is noted that instead of using a separate vacuum sleeve 158 and outer sheath 160, these two elements can be integrated to form a single integrated part.

A lock anchor 162 of the cryosurgical probe 132 is securely positioned over the outer sheath 160. The lock anchor 162 provides for detachable connection to the fluid connector assembly 134. This connection may be provided for, by example, threads 164. A threaded extension 163 extends axially from a main portion 165 of the lock anchor 162. The threaded extension 163 has the external threads 164 and also internal threads 167. The internal threads 167 provide connection to the fluid delivery/return manifold assembly 152. The main portion 165 is securely attached to the outer sheath 160.

During operation, fluid is delivered through the fluid inlet conduit 142, through the fluid delivery section 154 of the fluid delivery/return manifold assembly 152, through the Joule-Thomson (J-T) port 153 at a distal end of the fluid delivery section 154 and is returned through the return manifold section 156 and delivered out of the cryosurgical probe 132 and through the fluid connector assembly 134. The insulative vacuum sleeve 158 is provided between the outer sheath 160 and the return manifold section 156 at a control region of the outer sheath proximal to a distally located treatment region of the outer sheath.

The fluid delivery/return manifold assembly 152 includes a high pressure stem 166 for receiving high pressure fluid from the fluid connector assembly 134. The high pressure stem 166 is an elongated element with a circular cross-section and having a proximal circumferential groove 168 and a distal circumferential groove 170. A low pressure seal 172 is positioned within the proximal circumferential groove 168 to provide sealing engagement with a low pressure portion of the connector assembly 134. A high pressure seal 174 is positioned within the distal circumferential groove to provide sealing engagement with a high pressure portion of the connector assembly 134. (The low pressure seal 172 actually sees both high pressure and low pressure.)

The fluid delivery/return manifold assembly 152 also includes an extension tube 176 and orifice tube 178. A first end of the extension tube 176 is secured within the high pressure stem 166. The second, opposite end is secured to the orifice tube 178. The distal end of the orifice tube 178 functions as the J-T port 153. A portion of the return fluid flow passageway is provided in a space formed between an inner surface of the vacuum sleeve 158 and an outer surface of the extension tube 176.

As can be seen in FIG. 10, the sheath 160 further contains a coil collector, i.e. copper wire 182, which cooperates with the sheath 160 to guide the return fluid from the J-T port 153 to the vacuum sleeve 158. The coil collector can be hand-formed or machine-formed.

Referring now to FIGS. 11 and 12, another embodiment of the cryosurgical probe system is illustrated, designated generally as 186. In this embodiment, the cryosurgical probe, designated generally as 188, includes two extension tubes 190,192 providing two J-T ports 192 for increased power. The J-T ports 192 may be made to be axially spaced. This provides the ability to create an elongated iceball although the desired elongation is typically provided by the desired positioning of the insulative vacuum sleeve 194.

Additionally, this embodiment illustrates that there are a variety of different locking mechanisms that may be used to contain the cryosurgical probe 188 within the connector assembly 196. Some of these locking mechanisms may be quick disconnect mechanisms. In this embodiment a push-button/pin assembly 198 is utilized. This assembly is in a normally locked position and unlocked upon application of the pushbutton 199.

Figure 13:
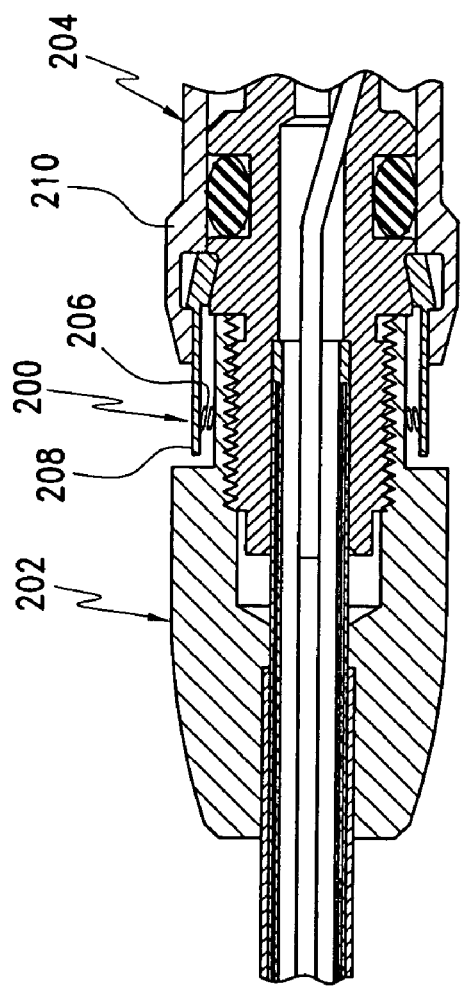
FIG. 13 is cross-sectional view of a portion of another embodiment in which a lever lock assembly is used to secure the connector assembly relative to the cryosurgical probe.

Obviously, there are a variety of different locking mechanisms that may be utilized. For example, referring now to FIG. 13 a lever lock assembly is illustrated, designated generally as 200, as a means for securing the cryosurgical probe 202 to a connector assembly 204. The lever lock assembly 200 includes a spring 206 for biasing a locking piece 208 that cooperates with a recessed area of a lock housing 210 of the connector assembly 204.

Figure 14:
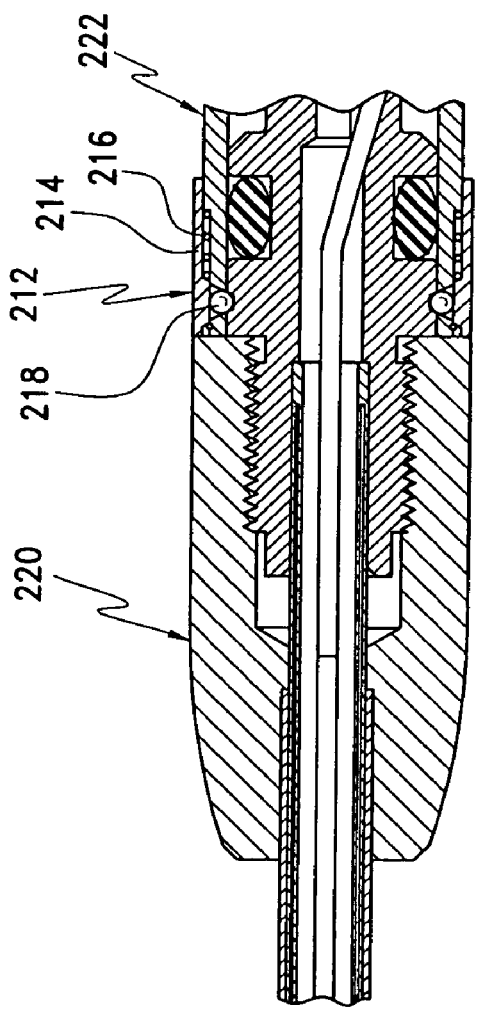
FIG. 14 is cross-sectional view of a portion of another embodiment in which a ball lock assembly is used to secure the connector assembly relative to the cryosurgical probe.

Referring now to FIG. 14 a ball lock assembly, designated generally as 212, is illustrated, in which a sleeve 214 is biased by a spring 216. This provides the desired securing of a locking element 218 within a recessed area of a cryosurgical probe, designated generally as 220. Locking of the cryosurgical probe 220 relative to the connector assembly 222 is thus provided. As noted above, the above-identified examples of attachment are shown by way of illustration. There are many other securing means that could be implemented.

Although the heat exchanger heretofore discussed is a finned cryostat it is understood that various other forms of heat exchangers may be utilized in lieu thereof. Referring now to FIG. 15 a tube-in-tube sintered cryostat 224 is illustrated. Tube-in-tube sintered cryostat 224 includes an inner tube 226 positioned within an outer tube 228. Sintered material 230, 232 is in both tubes 226, 228. Such sintered material may be, for example, stranded copper alloy wire. The outer tube 228 serves to provide access for inlet gas 229 while the inner tube 230 provides access for outlet gas 231. Use of cryostat 224 may minimize labor and part costs.

Referring now to FIG. 16 a threaded cryostat 234 is illustrated. In this instance an inner tube 236 is positioned within an outer tube 238. A threaded element 240 is positioned between the outer tube 238 and the inner tube 236. The threaded element 240 has exterior threads and interior threads that provide heat exchange for inlet gas 242 and outlet gas 244. This approach may also provide reduced labor and part costs. It is noted that this can be alternatively be implemented so that inlet gas may be introduced between the inner tube 236 and the interior threads. Outlet gas flows between the outer tube 238 and the exterior threads. The threaded element 240 is preferably formed of highly thermally conductive and high strength material such as copper alloy material.

In certain instances the interior threads of the threaded element 240 may be eliminated and substituted with an inner tube 236 that is formed of sintered metal or a metal coil.

Referring now to FIG. 17 a coiled/sintered cryostat is illustrated, designated generally as 246. This heat exchanger includes an inner tube 248 positioned within an outer tube 250. Sintered material 252 is provided in the space formed between the concentric tubes 248, 250. A coil 254 is located in that space within the sintered material 252. This approach may also provide beneficial labor and part costs. Additionally, it maximizes heat exchange efficiency.

Figure 18:
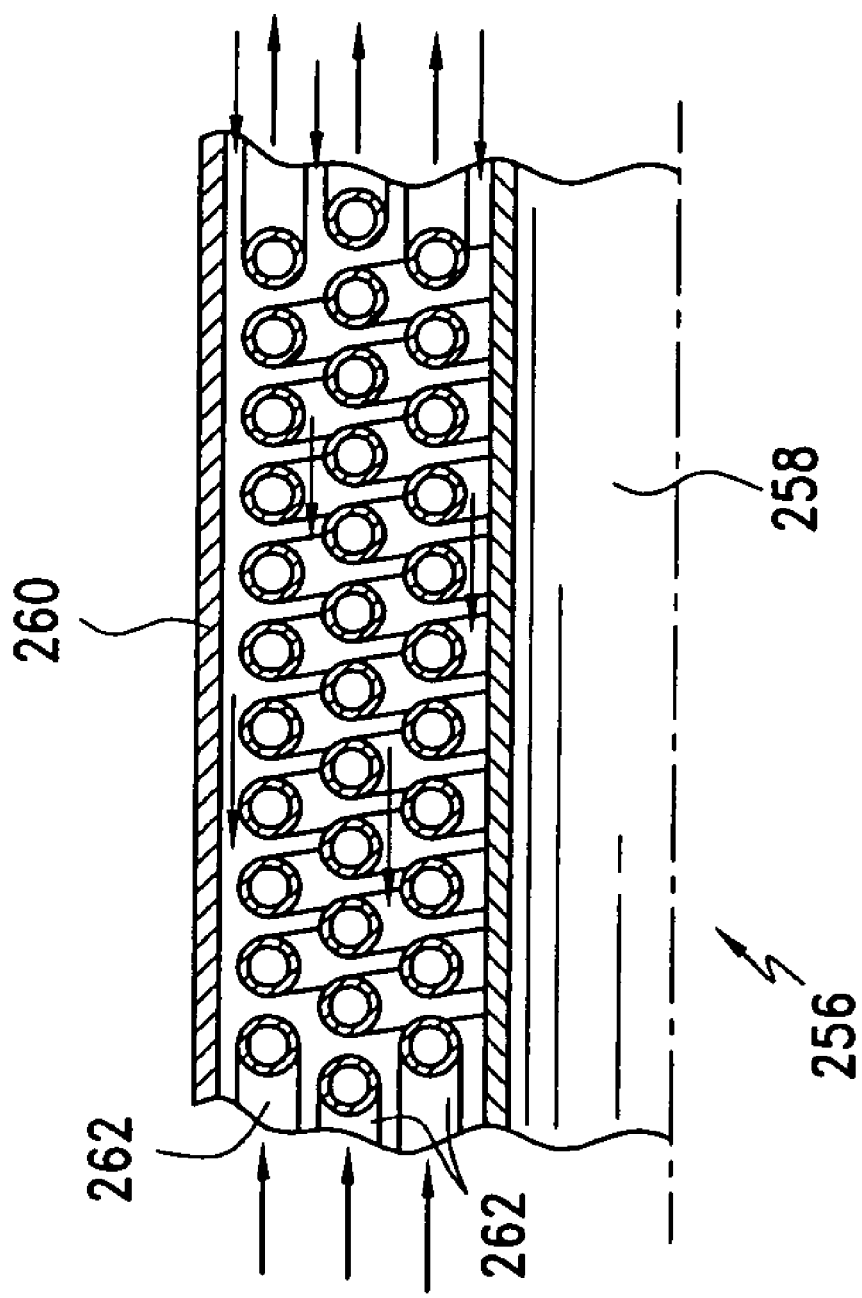
FIG. 18 is a cross-sectional view of a portion of a stacked coil cryostat.

Referring now to FIG. 18 a stacked coil cryostat is illustrated, designated generally as 256. This heat exchanger includes an inner tube 258 positioned within an outer tube 260. Stacked coils 262 are provided in the space formed between the concentric tubes 258, 260. The coils 262 may be formed of, for example, copper alloy material. This embodiment has the advantage of minimal material costs. It is noted that in all of the embodiments described relative to FIGS. 15–18 the fluid directions can be reversed depending on the particular design constraints.

Thus, while the preferred embodiments of the devices and methods have been described in reference to the environment in which they were developed, they are merely illustrative of the principles of the invention.

For example, the use of a manifold-system hose 22 and manifold 24 may not be included. In such instance, for example, a manifold-fluid connector assembly hose 28 with connector 38 would be replaced with a fluid supply line that connects the connector assembly 30 directly at an inlet section 14 to a source 16 of cryogenic fluid.

Further, although the cryostat 94 has been shown positioned within the manifold-fluid connector assembly hose 28 it may be positioned in other locations, notably, for example, in the manifold 24 or within the source 16.

Although the cryosurgical probe system is particularly advantageous for radiological applications it is also advantageous for many other types of ablation applications, such as prostate cryosurgery and other operating room based procedures.

Other embodiments and configurations may be devised without departing from the spirit of the invention and the scope of the appended claims.

The invention claimed is:

1. A cryosurgical probe system, comprising:
   a. a fluid supply line connectable at an inlet section to a source of cryogenic fluid;
   b. a fluid connector assembly securely connected to an outlet section of said fluid supply line for receiving fluid from said outlet section of said fluid supply line, said fluid connector assembly comprising:
      i. a substantially cylindrical lock housing securely attached to said outlet section of said fluid supply line, said lock housing having a fluid inlet conduit for receiving high pressure fluid from said fluid supply line and a fluid outlet conduit for transferring return fluid from a cryosurgical probe to said fluid supply line; and,
      ii. a locking mechanism positioned at a locking portion of said lock housing to provide detachable engagement of a cryosurgical probe positioned therein and,
   c. a detachable cryosurgical probe detachably connectable to said fluid connector assembly, said cryosurgical probe for receiving fluid from said fluid connector assembly and manipulating said fluid to provide suitable temperatures for cryosurgical treatment, said detachable cryosurgical probe, comprising:
      i. a fluid delivery/return manifold assembly comprising a fluid delivery section and a return manifold section, said return manifold section positioned over a portion of said fluid delivery section, said return manifold section comprising an insulative vacuum sleeve, said fluid delivery/return manifold assembly having a proximal end section;
      ii. an outer sheath securely positioned over said vacuum sleeve and extending from said fluid delivery/return manifold assembly; and,
      iii. a lock anchor securely positioned over said outer sheath, said lock anchor for detachable connection to said fluid connector assembly,
   wherein during operation fluid is delivered through said fluid delivery/return manifold assembly, through a Joule-Thomson (J-T) port defined at a distal end of said fluid delivery section and is returned through said return manifold section and delivered out of said cryosurgical probe, said insulative vacuum sleeve being provided between said outer sheath and said return manifold section at a control region of said outer sheath proximal to a distally located treatment region of said outer sheath.

2. The cryosurgical probe system of claim 1, wherein said locking mechanism comprises internal threads for attachment of the cryosurgical probe.

3. The cryosurgical probe system of claim 1, wherein said locking mechanism comprises a pushbutton/pin assembly for attachment of the cryosurgical probe.

4. The cryosurgical probe system of claim 1, wherein said locking mechanism comprises a quick disconnect assembly.

5. The cryosurgical probe system of claim 1, wherein said locking mechanism comprises a lever assembly.

6. The cryosurgical probe system of claim 1, wherein said locking mechanism comprises a ball lock assembly.

7. The cryosurgical probe system of claim 1, wherein said lock housing includes an axially extending boss.

8. The cryosurgical probe system of claim 1, wherein said fluid delivery/return manifold assembly comprises:
   a. a high pressure stem for receiving high pressure fluid from the fluid connector assembly; and,
   b. an extension tube having a first end and a second end, said first end being secured within the high pressure stem; and,
   said vacuum sleeve being secured at a first end to said high pressure stem, a portion of the return fluid flow passageway being provided in a space formed between an inner surface of said vacuum sleeve and an outer surface of said extension tube.

9. The cryosurgical probe system of claim 8, wherein said fluid delivery/return manifold assembly further comprises:
   an orifice tube secured to said second end of said extension tube, said orifice tube being in fluid communication with said extension tube, said orifice tube having said J-T port at a distal end thereof.

10. The cryosurgical probe system of claim 1, wherein said fluid delivery/return manifold assembly, comprises:
    a. a high pressure stem for receiving high pressure fluid from the fluid connector assembly,
       i. an elongated element having a circular cross-section, said elongated element having a proximal circumferential groove and a distal circumferential groove;
       ii. a low pressure seal positioned within said proximal circumferential groove to provide sealing engagement with a low pressure portion of said connector assembly
       iii. a high pressure seal positioned within said distal circumferential groove to provide sealing engagement with a high pressure portion of said connector assembly; and,
    b. an extension tube having a first end and a second end, said first end being secured within the high pressure stem,
    said vacuum sleeve being secured at a first end to said high pressure stem, a portion of the return fluid flow passageway being provided in a space formed between an inner surface of said vacuum sleeve and an outer surface of said extension tube.

11. The cryosurgical probe system of claim 10, wherein said fluid delivery/return manifold assembly further comprises an orifice tube secured to said second end of said extension tube, said orifice tube being in fluid communication with said extension tube, said orifice tube having said J-T port at a distal end thereof.

12. The cryosurgical probe system of claim 10, wherein said outer sheath, comprises:
    a cylindrical tube having a closed distal end.

13. The cryosurgical probe system of claim 12, wherein said outer sheath further includes the coil collector which cooperates with said sheath to guide the return fluid from the J-T port to said vacuum sleeve.

14. The cryosurgical probe system of claim 1, wherein said fluid connector assembly comprises:
    a. a substantially cylindrical lock housing having an extending boss securely attached to said outlet section of said fluid supply line, said lock housing having a fluid inlet conduit for receiving high pressure fluid from said fluid supply line and a fluid outlet conduit for transferring return fluid from said cryosurgical probe to said fluid supply line; and,
    b. a locking mechanism positioned at a locking portion of said lock housing to provide detachable engagement of a cryosurgical probe positioned therein.

15. The cryosurgical probe system of claim 14, wherein said lock housing and said extending boss are at substantially 90 degrees relative to each other.

16. The cryosurgical probe system of claim 14, wherein said lock housing and said extending boss are positioned at an angle from between about 0 degrees and 180 degrees relative to each other.

17. The cryosurgical probe system of claim 14, wherein said lock housing and said extending boss are positioned at an angle from between about 80 degrees and 140 degrees relative to each other.

18. The cryosurgical probe system of claim 1, wherein said fluid supply line comprises a cryostat assembly positioned adjacent to said outlet section of said fluid supply line, said cryostat assembly for receiving cryogenic fluid and providing heat exchange with fluid returning from said detachable cryosurgical probe.

19. The cryosurgical probe system of claim 1, wherein said fluid supply line comprises a cryostat assembly positioned adjacent to said outlet section of said fluid supply line, said cryostat assembly for receiving cryogenic fluid and providing heat exchange with fluid returning from said detachable cryosurgical probe, said cryostat assembly comprising at least one cryostat.

20. The cryosurgical probe system of claim 1, wherein said fluid supply line comprises a cryostat assembly positioned adjacent to said outlet section of said fluid supply line, said cryostat assembly for receiving cryogenic fluid and providing heat exchange with fluid returning from said detachable cryosurgical probe, said cryostat assembly comprising a plurality of cryostats.

21. The cryosurgical probe system of claim 1, wherein said fluid supply line comprises a cryostat assembly positioned adjacent to said outlet section of said fluid supply line, said cryostat assembly for receiving cryogenic fluid and providing heat exchange with fluid returning from said detachable cryosurgical probe, said cryostat assembly comprising a tube-in-tube sintered cryostat.

22. The cryosurgical probe system of claim 1, wherein said fluid supply line comprises a cryostat assembly positioned adjacent to said outlet section of said fluid supply line, said cryostat assembly for receiving cryogenic fluid and providing heat exchange with fluid returning from said detachable cryosurgical probe, said cryostat assembly comprising a threaded cryostat.

23. The cryosurgical probe system of claim 1, wherein said fluid supply line comprises a cryostat assembly positioned adjacent to said outlet section of said fluid supply line, said cryostat assembly for receiving cryogenic fluid and providing heat exchange with fluid returning from said detachable cryosurgical probe, said cryostat assembly comprising a coiled/sintered cryostat.

24. The cryosurgical probe system of claim 1, wherein said fluid supply line comprises a cryostat assembly positioned adjacent to said outlet section of said fluid supply line, said cryostat assembly for receiving cryogenic fluid and providing heat exchange with fluid returning from said detachable cryosurgical probe, said cryostat assembly comprising a stacked coil cryostat.

25. The cryosurgical probe system of claim 1, wherein said fluid supply line comprises a cryostat positioned therein for delivering fluid from the fluid supply line to said fluid connector assembly.

26. The cryosurgical probe system of claim 1, wherein said outlet section of said fluid supply line and a longitudinal axis of said cryosurgical probe are at substantially 90 degrees relative to each other.

27. The cryosurgical probe system of claim 1, wherein said outlet section of said fluid supply line and a longitudinal axis of said cryosurgical probe are positioned at an angle from between about 0 degrees and 180 degrees relative to each other.

28. The cryosurgical probe system of claim 1, wherein said outlet section of said fluid supply line and a longitudinal axis of said cryosurgical probe are positioned at an angle from between about 80 degrees and 140 degrees relative to each other.

29. The cryosurgical probe system of claim 1, wherein said cryogenic fluid comprises argon.

30. The cryosurgical probe system of claim 1, wherein said cryogenic fluid comprises nitrogen.

31. The cryosurgical probe system of claim 1, wherein said fluid supply line is connectable to a fluid source of a type that warms while undergoing Joule-Thomson expansion.

32. The cryosurgical probe system of claim 1, further comprising an MRI system for guidance.

33. The cryosurgical probe system of claim 1, wherein said detachable cryosurgical probe further includes means for warming.

34. The cryosurgical probe system of claim 1, wherein said detachable cryosurgical probe further includes means for warming, said means for warming comprising electrical heating means.

35. The cryosurgical probe system of claim 1, wherein said detachable cryosurgical probe further includes means for warming, said means for warming comprising RF heating means.

36. The cryosurgical probe system of claim 1, wherein said fluid connector assembly comprises a thermocouple secured therein for providing temperature data.

37. The cryosurgical probe system of claim 1, wherein said detachable cryosurgical probe comprises a malleable segment.

38. The cryosurgical probe system of claim 1, wherein said detachable cryosurgical probe comprises a bellows portion.

39. The cryosurgical probe system of claim 1 comprising a plurality of Joule-Thomson ports.

40. A detachable cryosurgical probe for connection to a fluid connector assembly of a detachable cryosurgical system, comprising:
  a. a fluid delivery/return manifold assembly comprising a fluid delivery section and a return manifold section, said return manifold section positioned over a portion of said fluid delivery section, said return manifold section comprising an insulative vacuum sleeve, said fluid delivery/return manifold assembly having a proximal end section;
  b. an outer sheath securely positioned over said vacuum sleeve and extending from said fluid delivery/return manifold assembly; and,
  c. a lock anchor securely positioned over said outer sheath, said lock anchor for detachable connection to a fluid connector assembly of a detachable cryosurgical system, wherein during operation fluid is delivered through said fluid delivery/return manifold assembly, through a Joule-Thomson (J-T) port defined at a distal end of said fluid delivery section and is returned through said return manifold section and delivered out of said cryosurgical probe, said insulative vacuum sleeve being provided between said outer sheath and said return manifold section at a control region of said outer sheath proximal to a distally located treatment region of said outer sheath.

41. The detachable cryosurgical probe of claim 40, wherein said fluid delivery/return manifold assembly comprises:
  a. a high pressure stem for receiving high pressure fluid from the fluid connector assembly; and,
  b. an extension tube having a first end and a second end, said first end being secured within the high pressure stem;
  said vacuum sleeve being secured at a first end to said high pressure stem, a portion of the return fluid flow passageway being provided in a space formed between an inner surface of said vacuum sleeve and an outer surface of said extension tube.

42. The detachable cryosurgical probe of claim 41, wherein said fluid delivery/return manifold assembly further comprises:
  an orifice tube secured to said second end of said extension tube, said orifice tube being in fluid communication with said extension tube, said orifice tube having said J-T port at a distal end thereof.

43. The detachable cryosurgical probe of claim 40, wherein said fluid delivery/return manifold assembly comprises:
  a. a high pressure stem for receiving high pressure fluid from the fluid connector assembly, said high pressure stem comprising:
    i. an elongated element having a circular cross-section, said elongated element having a proximal circumferential groove and a distal circumferential groove;
    ii. a low pressure seal positioned within said proximal circumferential groove to provide sealing engagement with a low pressure portion of said connector assembly;
    iii. a high pressure seal positioned within said distal circumferential groove to provide sealing engagement with a high pressure portion of said connector assembly; and,
  b. an extension tube having a first end and a second end, said first end being secured within the high pressure stem; and,
  said vacuum sleeve being secured at a first end to said high pressure stem, a portion of the return fluid flow passageway being provided between a space formed between an inner surface of said vacuum sleeve and an outer surface of said extension tube.

44. The detachable cryosurgical probe of claim 43 wherein said fluid delivery/return manifold assembly further comprises:
  an orifice tube secured to said second end of said extension tube, said orifice tube being in fluid communication with said extension tube, said orifice tube having said J-T port at a distal end thereof.

45. The detachable cryosurgical probe of claim 40, wherein said outer sheath, comprises:
  a cylindrical tube having a closed distal end.

46. The detachable cryosurgical probe of claim 40, wherein said lock anchor, comprises:

a. a main portion; and, b. a threaded extension extending axially from said main portion, said threaded extension comprising external threads and internal threads, said external threads for attachment to said connector assembly and said internal threads for connection to said fluid delivery/return manifold assembly, wherein said main portion is securely attached to said outer sheath.

47. The detachable cryosurgical probe of claim 40, wherein said lock anchor, comprises a quick disconnect mechanism.

48. The detachable cryosurgical probe of claim 40, wherein said lock anchor, comprises a quick disconnect mechanism comprising a pushbutton/pin assembly.

49. The detachable cryosurgical probe of claim 40, wherein said sheath contains a coil collector having a copper wire that cooperates with said sheath to guide the return fluid from the J-T port to said vacuum sleeve.

50. The detachable cryosurgical probe of claim 40, comprising a plurality of Joule-Thomson ports.

* * * * *

UNITED STATES PATENT AND TRADEMARK OFFICE
CERTIFICATE OF CORRECTION

| | |
|---|---|
| PATENT NO. | : 7,160,291 B2 |
| APPLICATION NO. | : 10/828031 |
| DATED | : January 9, 2007 |
| INVENTOR(S) | : Sanford D. Damasco |

It is certified that error appears in the above-identified patent and that said Letters Patent is hereby corrected as shown below:

Column 11, Line 59 Claim 13 - delete "the coil collector" and insert therefor --a coil collector--

Signed and Sealed this

Nineteenth Day of August, 2008

JON W. DUDAS
*Director of the United States Patent and Trademark Office*